(12) United States Patent
Graupe et al.

(10) Patent No.: US 8,658,138 B2
(45) Date of Patent: Feb. 25, 2014

(54) FOAMABLE COMPOSITION ESSENTIALLY FREE OF PHARMACEUTICALLY ACTIVE INGREDIENTS FOR THE TREATMENT OF HUMAN SKIN

(75) Inventors: Klaus Graupe, Berlin (DE); Gerald Städtler, Berlin (DE)

(73) Assignee: Intendis GmbH, Berlin (DE)

( * ) Notice: Subject to any disclaimer, the term of this patent is extended or adjusted under 35 U.S.C. 154(b) by 387 days.

(21) Appl. No.: 12/646,013

(22) Filed: Dec. 23, 2009

(65) Prior Publication Data

US 2010/0247449 A1 Sep. 30, 2010

Related U.S. Application Data

(60) Provisional application No. 61/140,152, filed on Dec. 23, 2008.

(30) Foreign Application Priority Data

Dec. 23, 2008 (EP) .................................... 08022333

(51) Int. Cl.
*A61K 9/12* (2006.01)
(52) U.S. Cl.
USPC ........................................................... 424/45

(58) Field of Classification Search
USPC ............................................................ 424/45
See application file for complete search history.

(56) References Cited

U.S. PATENT DOCUMENTS

| 6,423,323 B2 | 7/2002 | Neubourg |
| 2006/0275218 A1 | 12/2006 | Tamarkin et al. |
| 2007/0020213 A1 | 1/2007 | Tamarkin et al. |
| 2008/0044444 A1 | 2/2008 | Tamarkin et al. |

FOREIGN PATENT DOCUMENTS

| WO | WO-2005 018530 | 3/2005 |
| WO | WO 2008/038140 | 4/2008 |
| WO | WO-2008 038140 | 4/2008 |

OTHER PUBLICATIONS

European Search Report for EP 08 02 2333 dated Jul. 15, 2009.

*Primary Examiner* — Blessing M Fubara
*Assistant Examiner* — Jennifer Berrios
(74) *Attorney, Agent, or Firm* — Millen, White, Zelano, Branigan, P.C.

(57) ABSTRACT

The present invention related to the use of a pharmaceutical composition which is essentially free of pharmaceutically active ingredients for the treatment of human skin, especially in the treatment of rosacea, acne, atopic dermatitis, contact dermatitis, perioral dermatitis, psoriasis or neurodermitis, as well as for prophylactic and/or cosmetic purposes.

10 Claims, 4 Drawing Sheets

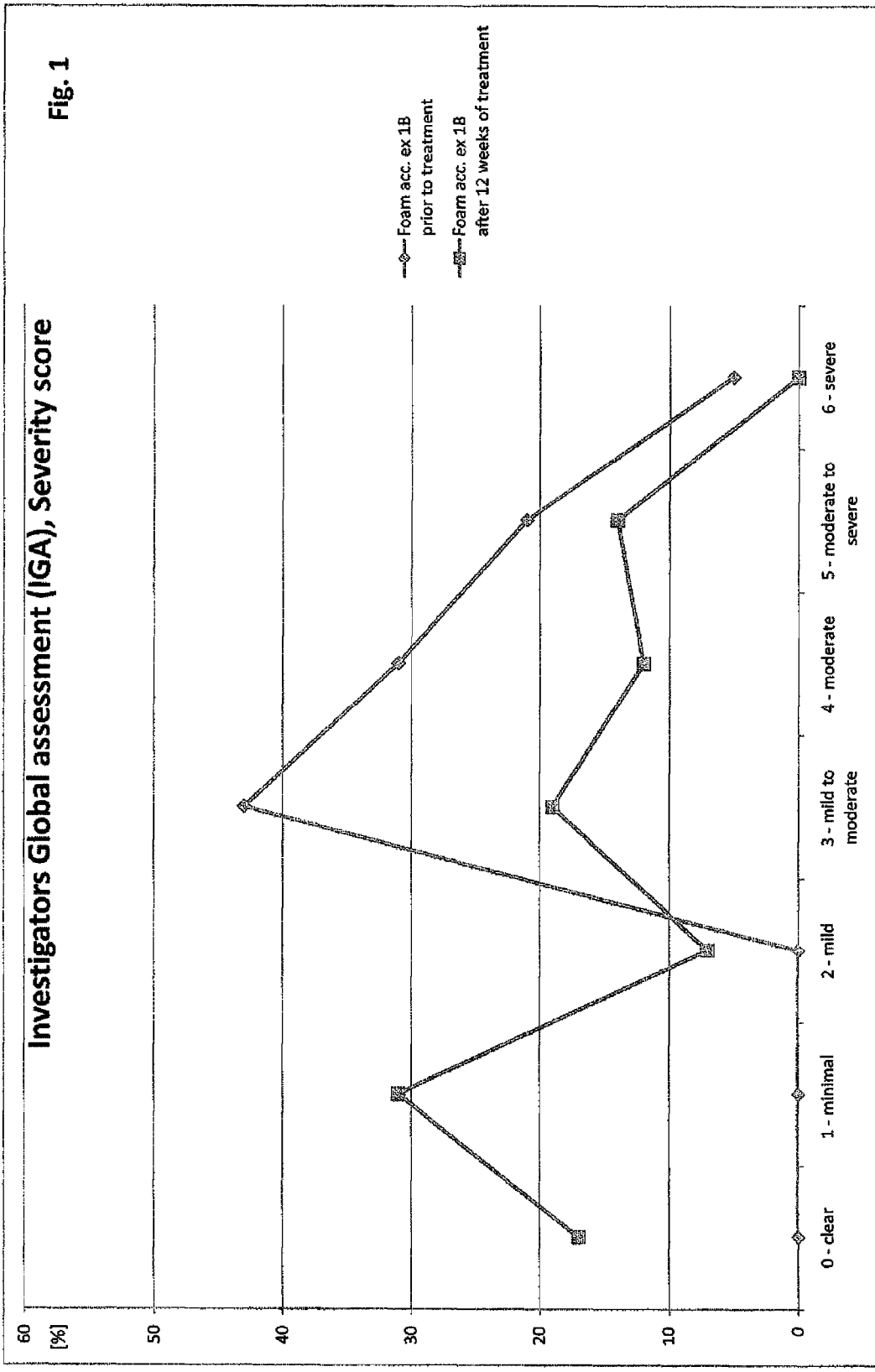

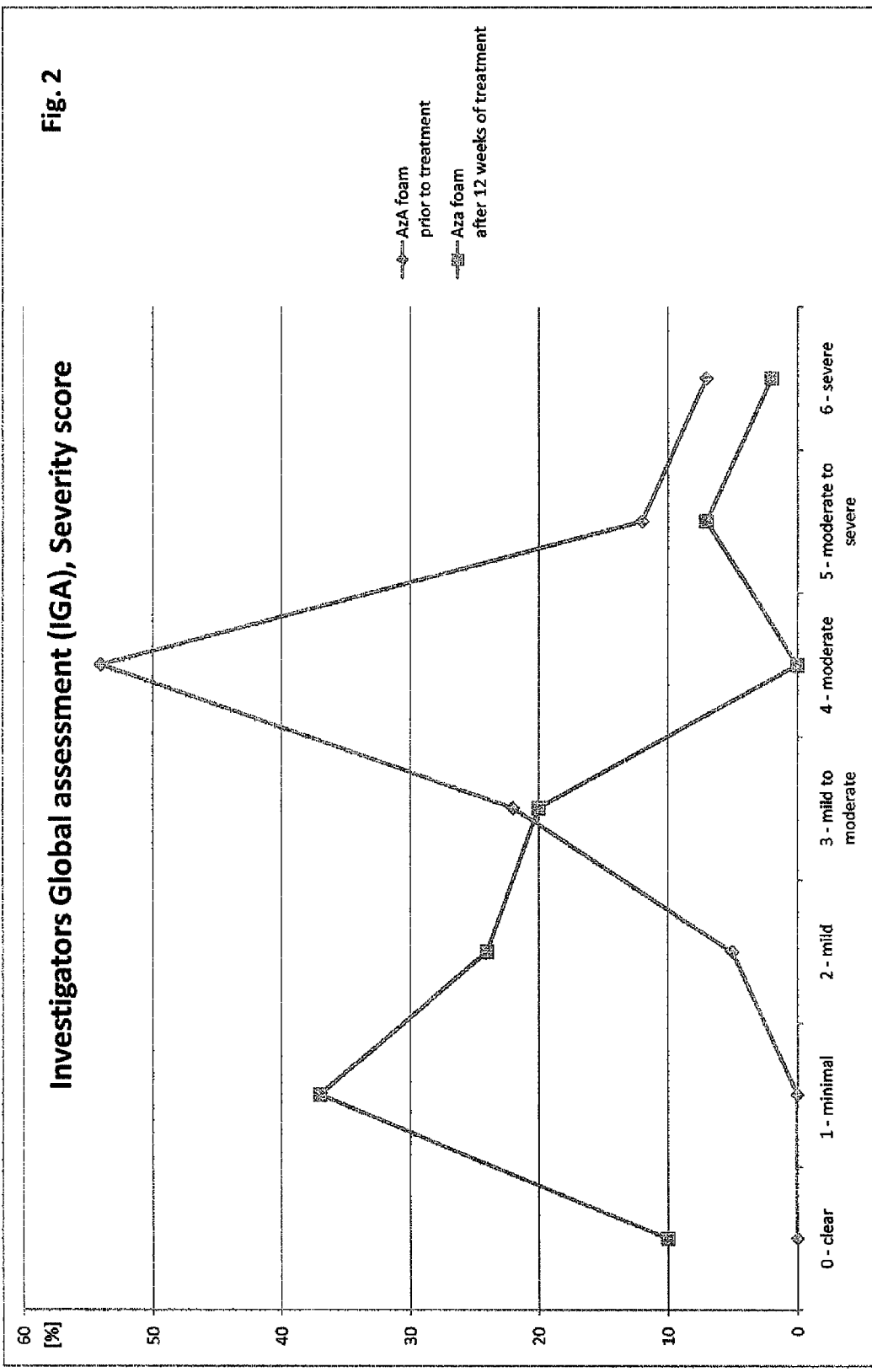

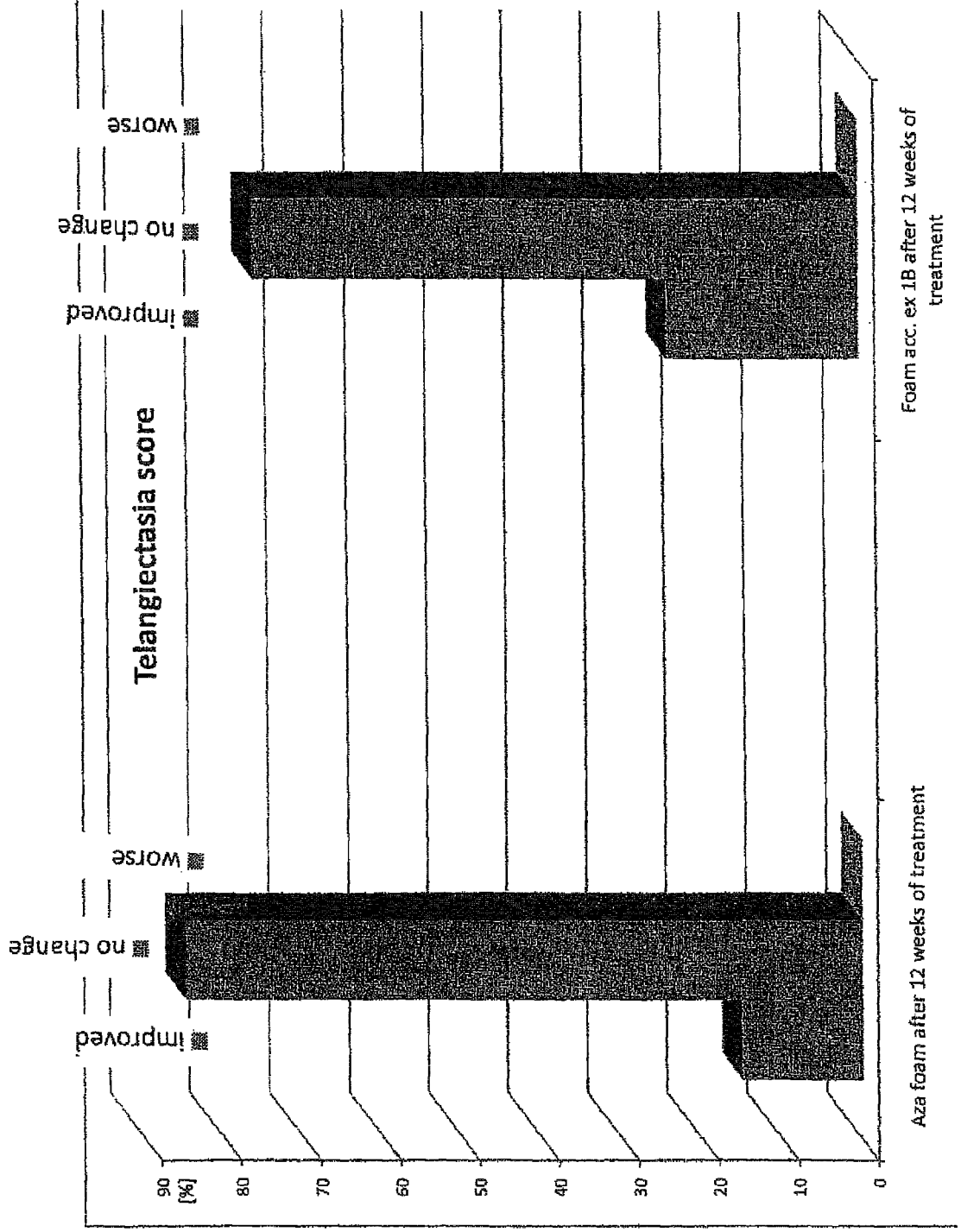

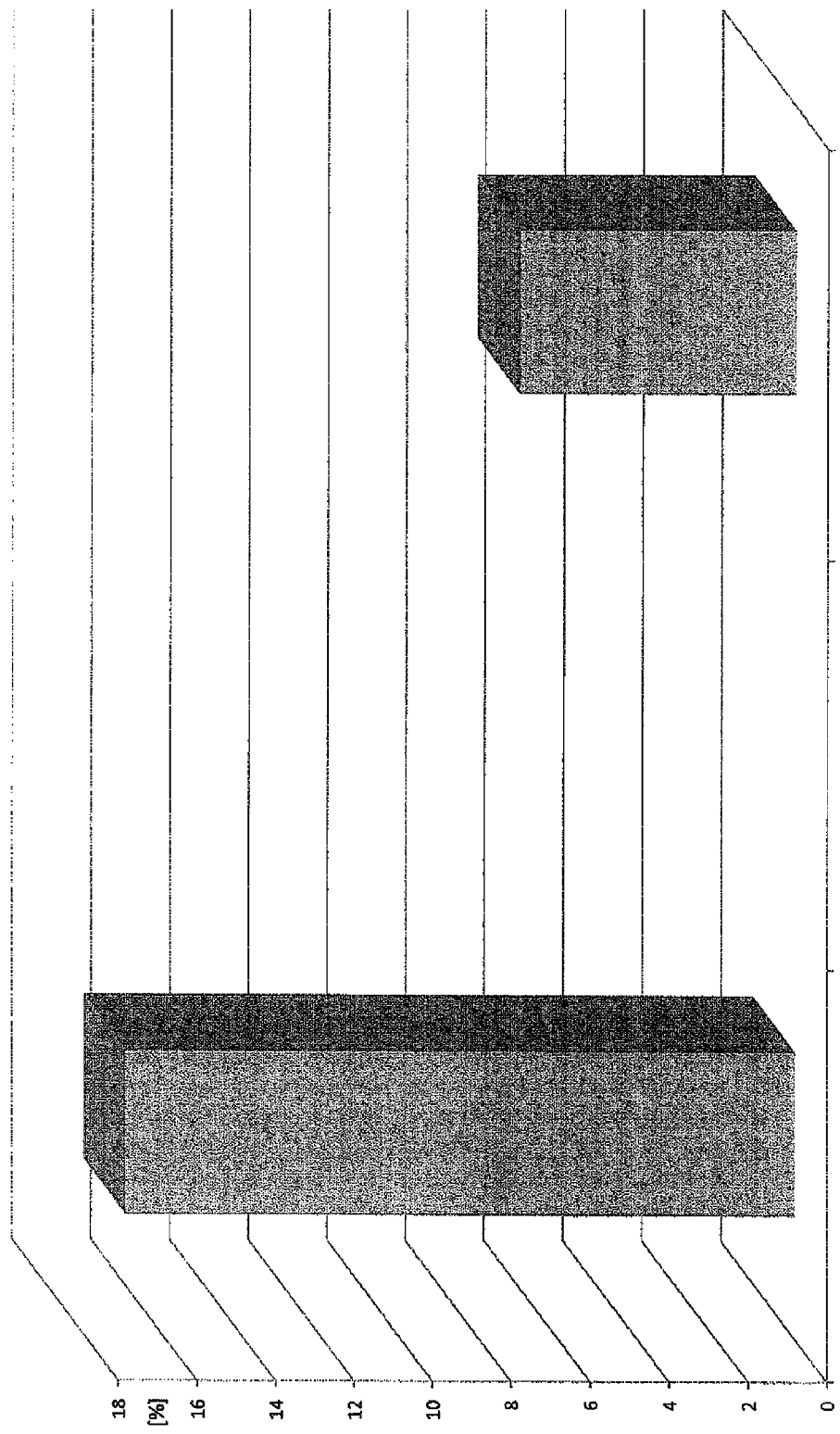

FOAMABLE COMPOSITION ESSENTIALLY FREE OF PHARMACEUTICALLY ACTIVE INGREDIENTS FOR THE TREATMENT OF HUMAN SKIN

This application claims the priority according to the Paris Convention of the European Patent application EP 0802233.2 (filing date: Dec. 23, 2008) as well as all benefits from earlier U.S. application Ser. No. 61/140,152 (filing date: Dec. 23, 2008), which are both incorporated herein by reference.

BACKGROUND AND STATE OF THE ART

A number of foamable compositions containing pharmaceutically active ingredients is known in the art for the treatment of various medical conditions of the skin or of body cavities. The state of the art includes WO2005/018530, WO 2008/038140, US 2008/044444, US 2006/275218, US 2007/020213, US 2002/001599, WO 2004/037225, WO 2005/011567, US 2005/0232869, US 2005/0069566, and others, which are all incorporated herein by reference. These foamable compositions and foam carriers have been developed as they can contain a number of pharmaceutical ingredients for the treatment of a variety of diseases of the skin or of body cavities. These foams are easy to apply to the skin and do avoid stinging and drying, properties that have been reported from previous foam compositions. However, all of these compositions do require the presence of one or more pharmaceutically active agents such as anti-inflammatory agents (e.g. COX-1 inhibitors, COX-2 inhibitors, salicylic acid derivatives, dicarboxylic acids or dicarboxylic acid derivatives, THF-$\alpha$ agents, immunosupressant agents, immunoregulating agents, glucocorticoids, steroids or others). It is needless to state that the need for pharmaceutically active agents is a disadvantage, as such agents may have unwanted side effects at least with some of the patients.

GENERAL DESCRIPTION OF THE INVENTION

It has now been found, that surprisingly a foamable composition which is essentially free of pharmaceutically active ingredients, consisting of
 (a) at least one emollient,
 (b) at least one stabilizer,
 (c) at least one preservative,
 (d) at least one emulsifier,
 (e) at least one foam stabilizer,
 (f) at least one moisturizer
 together with a propellant,
can be used for the treatment of human skin especially for the treatment of rosacea, acne, atopic dermatitis, contact dermatitis, perioral dermatitis, psoriasis or neurodermitis.

A preferred embodiment of the invention is the use of a foamable composition essentially free of pharmaceutically active ingredients as described before, wherein
 (a) at least one emollient is caprylic/capric triglyceride,
 (b) at least one stabilizer cetostearyl alcohol or glyceryl stearate or a mixture thereof,
 (c) at least one preservative is benzoic acid,
 (d) at least one emulsifier is PEG-40 stearate, polysorbate 80 or a mixture thereof,
 (e) at least one foam stabilizer is methylcellulose, xanthan gum or a mixture thereof,
 (f) at least one moisturizer is dimethyl isosorbide, propylene glycol or a mixture thereof together with a propellant for the treatment of human skin especially for the treatment of rosacea, acne, atopic dermatitis, contact dermatitis, perioral dermatitis, psoriasis or neurodermitis.

An especially preferred embodiment of the invention is the use of a foamable composition essentially free of pharmaceutically active ingredients as described before, containing
 (a) caprylic/capric triglyceride in an amount of about 10.87 weight percent,
 (b) a mixture of about 1.09 weight percent cetostearyl alcohol and about 0.54 weight percent glyceryl stearate,
 (c) benzoic acid in an amount of at least one preservative is about 0.1 weight percent,
 (d) a mixture of about 2.83 weight percent PEG-40 stearate and about 0.98 weight percent polysorbate 80,
 (e) a mixture of about 0.11 weight percent methylcellulose and about 0.27 weight percent xanthan gum,
 (f) a mixture of about 5.44 weight percent dimethyl isosorbide and about 10.87 weight percent propylene glycol together with a propellant for the treatment of human skin especially for the treatment of rosacea, acne, atopic dermatitis, contact dermatitis, perioral dermatitis, psoriasis or neurodermitis.

As propellant a compound may be used, which is a gas at room temperature under normal pressure and which may be liquidified at increased pressure at room temperature. Useful propellants are butane, propane, isobutene, dimethylether, fluorocarbon gases or mixtures thereof.

The term "pharmaceutically active compounds" or "pharmaceutically active ingredients" refers to compounds with proved pharmaceutical activity demonstrated in clinical trials and approved as a drug by the European Medicines Agency (EMEA) or the US Food and Drug Administration (FDA). The term "essentially free of pharmaceutically active compounds" or "essentially free of pharmaceutically active ingredients" means that no "pharmaceutically active compound" or "pharmaceutically active ingredient" has been intended to be added to the composition. The total amount of pharmaceutically active ingredients as a result of unintended contamination is therefore well below 0.05%, preferably below 0.01%. Most preferred is a composition in which no amount of any pharmaceutical ingredient can be detected with standard analytical methods used in pharmaceutical technology.

The foamable compositions according to the invention are manufactured according to the methods described in the art which are known to a pharmaceutical expert. They are usually packed in a container with an outlet valve. Possible containers in valves are likewise described in the art and do not need to be explained in this document.

The foamable composition is substantially alcohol-free, i.e., free of short chain alcohols (with 1-4 carbon atoms chain length).

One known disadvantage of state of the art compositions is the low solubility of the pharmaceutically active compounds. It is therefore an advantage of the compositions according to the present inventions that there is no need to solve any pharmaceutically active compounds.

In clinical tests it has been shown that foamable compositions according to the description provided herein have beneficial properties, especially in the treatment of rosacea. It was very surprising to note that this therapeutic effect has been achieved without application of any pharmaceutically active ingredient. A number of further medical conditions can be treated with the composition according to the present invention such as acne, atopic dermatitis, contact dermatitis, perioral dermatitis, psoriasis and neurodermitis.

Furthermore the compositions described herein may be used for a prophylactic treatment of the human skin (e.g. in patients with a known tendency to develop such disease).

The foamable composition compositions according to the description provided herein may also be used for a cosmetic treatment of the human skin.

It is therefore another aspect of the invention to provide a method of treating human skin disorders such as acne, atopic dermatitis, contact dermatitis, perioral dermatitis, psoriasis and neurodermitis by topical application of a foam as described herein to a patient in need thereof.

FIG. 1 depicts Investigators Global Assessment (IGA) scores for a foam composition according to the invention before and after treatment.

FIG. 2 depicts Investigators Global Assessment (IGA) scores for a comparison foam composition before and after treatment.

FIG. 3 depicts an investigators telangiectasia assessment after a 12 week study.

FIG. 4 compares a prior art composition to a composition according to the present invention.

It is a further aspect of the invention to provide a method of prophylactic treatment of human skin, especially for humans with a known tendency to develop skin disorders such as acne, atopic dermatitis, contact dermatitis, perioral dermatitis, psoriasis and neurodermitis by topical application of a foam as described herein to such human.

It is a still further aspect of the invention to provide a method of cosmetic treatment of human skin by topical application of a foam as described herein to a human.

For all of these applications described herein (therapeutic, prophylactic or cosmetic) the following compositions essentially free of active pharmaceutical compounds packed in a container with an outlet valve have been found to be most useful

| | |
|---|---|
| 10.00-12.00 g/100 g | Caprylic/capric triglyceride |
| 0.90-1.20 g/100 g | Cetostearyl alcohol |
| 0.44-0.70 g/100 g | Glyceryl stearate |
| 0.10-0.15 g/100 g | Benzoic acid |
| 2.50-3.00 g/100 g | PEG-40 stearate |
| 0.08-0.20 g/100 g | Methylcellulose |
| 0.20-0.32 g/100 g | Xanthan gum |
| 0.90-1.20 g/100 g | Polysorbate 80 |
| 5.35-6.00 g/100 g | Dimethyl isosorbide |
| 10.87-12.25 g/100 g | Propylene glycol |
| to pH 4.5 | Sodium hydroxide |
| ad 100 | Purified water |
| 7.00-9.00 g | Propellant blend |

EXAMPLES

Example 1

The following compositions are prepared according to methods known in the art.

| Ingredient | Function | [g/100 g] A | [g/100 g] B | [g/100 g] C | [g/100 g] D | [g/100 g] E |
|---|---|---|---|---|---|---|
| Caprylic/capric triglyceride | Emollient | 10.00 | 10.87 | 11.10 | 12.00 | 11.50 |
| Cetostearyl alcohol | Stabilizer | 1.20 | 1.09 | 0.90 | 1.00 | 1.20 |
| Glyceryl stearate | Stabilizer | 0.44 | 0.54 | 0.60 | 0.55 | 0.70 |
| Benzoic acid | Preservative | 0.10 | 0.10 | 0.11 | 0.12 | 0.15 |
| PEG-40 stearate | Emulsifier | 3.00 | 2.83 | 2.50 | 2.60 | 2.95 |
| Methyl cellulose | Foam stabilizer | 0.08 | 0.11 | 0.15 | 0.18 | 0.20 |
| Xanthan gum | Foam stabilizer | 0.20 | 0.27 | 0.25 | 0.30 | 0.32 |
| Polysorbate 80 | Emulsifier | 1.00 | 0.98 | 0.90 | 0.95 | 1.20 |
| Dimethyl isosorbide | Moisturizer | 5.35 | 5.44 | 5.75 | 6.00 | 5.90 |
| Propylene glycol | Moisturizer | 12.00 | 10.87 | 11.80 | 12.25 | 11.50 |
| Sodium hydroxide | Neutralizer | to pH 4.5 | to pH 4.5 | to pH 4.5 | to pH 4.5 | to pH 4.5 |
| Purified water | External phase | ad 100 | ad 100 | ad 100 | ad 100 | ad 100 |
| | | 100.00 | 100.00 | 100.00 | 100.00 | 100.00 |
| Propellant blend | Foaming aid | 8.00 | 8.00 | 7.00 | 9.00 | 8.50 |
| Total | | 108.00 | 108.00 | 107.00 | 109.00 | 108.50 |

The composition according to example 1 B shows the most beneficial properties.

Example 2

Patients suffering from rosacea are treated with the compositions described in example 1. The particular composition is applied several times a day, preferably at least three times a day. After two weeks of application patients show significantly less symptoms of rosacea. The symptoms are further decreasing over time upon continuation of the application as described above. Especially patients with mild forms of rosacea do benefit from the application

Example 3

Patients suffering from psoriasis are treated with the composition according to the invention. The composition is applied several times a day, preferably at least three times a day. After two weeks of application patients show significantly less symptoms of psoriasis. The symptoms are further decreasing over time upon continuation of the application as described above.

Example 4

The use of the compositions according to example 1 has been compared to a prior art disclosure and the following data have been collected. It is believed that document US 2008/044444 is the closest prior art. Example 9 of US 2008/044444 discloses a dicarboxylic acid composition which is comparable to the composition of claim 1 but contains 15% azelaic acid. Azelaic acid is known to be effective in rosacea treatment. It is e.g. part of a gel formulation sold under the trademarks Finacea® and Skinoren Gel® and approved by various regulatory authorities including the FDA. Azelaic acid compositions such as Finacea are therefore considered as a standard therapy in the treatment of rosacea. US 2008/044444 describes quite a number of disorders treatable with the compositions of US 2008/044444 (see paragraph [0186]). There is, however, no specific data proving effectiveness of such composition in the treatment of any of the mentioned disorders.

The applicant has carried out clinical investigations comparing a composition as described herein with a prior art composition as described in example 9 of US 2008/044444. An azelaic acid containing foam composition according to example 9 of US 2008/044444 (hereinafter referred to as "Aza foam") has been studied in a 12 week exploratory, multicenter, double-blind study compared with a composition according to example 1b of the present application free of any pharmaceutically active ingredient. More than 80 patients have been treated: approximately 50% with the azelaic acid containing foam (Aza foam), the other 50% with the foam composition according to example 1b. The mentioned patients have been treated twice daily over 12 weeks topically. The results are presented in the annexed figures:

FIGS. 1 and 2 show Investigators Global Assessment (IGA) scores for the two compositions before and after treatment demonstrating the assessed severeness of the disease. The clinical investigators had to score the severeness of papulopustular rosacea before and after treatment. FIG. 1 shows the IGA score of the composition according to the invention, FIG. 2 the IGA score of the composition according to Example 9 of US 2008/044444. All data are provided as percentage of treated patients. FIGS. 1 and 2 indicate a comparable efficacy of both compositions: It has been found that a number of patients suffering from moderate to severe forms of papulopustular rosacea prior to treatment shifted to clear to mild forms. No statistically significant difference between the treatments has been found. This finding is surprising to the experts as azelaic acid is a well-recognized drug and a standard therapy in the treatment of rosacea. It was therefore quite surprising that a foamable composition according to example 1 of the present application free of azelaic acid shows comparable results.

Furthermore, a telangiectasia score has been measured during examination. Investigators have been asked to compare in the same randomized double-blind study the severeness telangiectasia intensity. At the end of the 12-weeks period the investigators have been asked to assess if the patients telangiectasia intensity had been improved, remained unchanged or worsened. The results are presented in FIG. 3. It is very surprising to note that the number of patients with improved telangiectasia score is much higher compared to treatment with the azelaic acid containing foam.

Furthermore, the number of adverse events (such as itching, stinging and burning) had been counted. Only mild or moderate adverse events have been reported, no serious adverse event had been reported during this clinical study. As demonstrated in FIG. 4, the total number of adverse events is significantly higher in the prior art composition comparing to the composition according to the invention.

The invention claimed is:

1. A method for the treatment or prophylaxis of rosacea, acne, atopic dermatitis, contact dermatitis, perioral dermatitis, psoriasis or neurodermitis, comprising topically applying a foamable composition consisting of:

| | |
|---|---|
| 10.00-12.00 g/100 g | Caprylic/capric triglyceride |
| 0.90-1.20 g/100 g | Cetostearyl alcohol |
| 0.44-0.70 g/100 g | Glyceryl stearate |
| 0.10-0.15 g/100 g | Benzoic acid |
| 2.50-3.00 g/100 g | PEG-40 stearate |
| 0.08-0.20 g/100 g | Methylcellulose |
| 0.20-0.32 g/100 g | Xanthan gum |
| 0.90-1.20 g/100 g | Polysorbate 80 |
| 5.35-6.00 g/100 g | Dimethyl isosorbide |
| 10.87-12.25 g/100 g | Propylene glycol |
| to pH 4.5 | Sodium hydroxide |
| ad 100 | Purified water |
| 7.00-9.00 g | Propellant blend | wherein said composition is dispensed from a container with an outlet valve.

2. A method according to claim 1, wherein said foamable composition consists of

| | |
|---|---|
| 10.00 g/100 g | Caprylic/capric triglyceride |
| 1.20 g/100 g | Cetostearyl alcohol |
| 0.44 g/100 g | Glyceryl stearate |
| 0.10 g/100 g | Benzoic acid |
| 3.00 g/100 g | PEG-40 stearate |
| 0.08 g/100 g | Methylcellulose |
| 0.20 g/100 g | Xanthan gum |
| 1.00 g/100 g | Polysorbate 80 |
| 5.35 g/100 g | Dimethyl isosorbide |
| 12.00 g/100 g | Propylene glycol |
| to pH 4.5 | Sodium hydroxide |
| ad 100 | Purified water |
| 8.00 g | Propellant blend | or consists of

| | |
|---|---|
| 10.87 g/100 g | Caprylic/capric triglyceride |
| 1.09 g/100 g | Cetostearyl alcohol |
| 0.54 g/100 g | Glyceryl stearate |
| 0.10 g/100 g | Benzoic acid |
| 2.83 g/100 g | PEG-40 stearate |
| 0.11 g/100 g | Methylcellulose |
| 0.27 g/100 g | Xanthan gum |
| 0.98 g/100 g | Polysorbate 80 |
| 5.44 g/100 g | Dimethyl isosorbide |
| 10.87 g/100 g | Propylene glycol |
| to pH 4.5 | Sodium hydroxide |
| ad 100 | Purified water |
| 8.00 g | Propellant blend | or consists of

| | |
|---|---|
| 11.10 g/100 g | Caprylic/capric triglyceride |
| 0.90 g/100 g | Cetostearyl alcohol |
| 0.60 g/100 g | Glyceryl stearate |
| 0.11 g/100 g | Benzoic acid |
| 2.50 g/100 g | PEG-40 stearate |
| 0.15 g/100 g | Methylcellulose |
| 0.25 g/100 g | Xanthan gum |
| 0.90 g/100 g | Polysorbate 80 |
| 5.75 g/100 g | Dimethyl isosorbide |
| 11.80 g/100 g | Propylene glycol |
| to pH 4.5 | Sodium hydroxide |
| ad 100 | Purified water |
| 7.00 g | Propellant blend | or consists of

| | |
|---|---|
| 12.00 g/100 g | Caprylic/capric triglyceride |
| 1.00 g/100 g | Cetostearyl alcohol |
| 0.55 g/100 g | Glyceryl stearate |
| 0.12 g/100 g | Benzoic acid |
| 2.60 g/100 g | PEG-40 stearate |
| 0.18 g/100 g | Methylcellulose |
| 0.30 g/100 g | Xanthan gum |
| 0.95 g/100 g | Polysorbate 80 |
| 6.00 g/100 g | Dimethyl isosorbide |
| 12.25 g/100 g | Propylene glycol |
| to pH 4.5 | Sodium hydroxide |
| ad 100 | Purified water |
| 9.00 g | Propellant blend | or consists of

| | |
|---|---|
| 11.50 g/100 g | Caprylic/capric triglyceride |
| 1.20 g/100 g | Cetostearyl alcohol |
| 0.70 g/100 g | Glyceryl stearate |
| 0.15 g/100 g | Benzoic acid |
| 2.95 g/100 g | PEG-40 stearate |
| 0.20 g/100 g | Methylcellulose |
| 0.32 g/100 g | Xanthan gum |
| 1.20 g/100 g | Polysorbate 80 |
| 5.90 g/100 g | Dimethyl isosorbide |
| 11.50 g/100 g | Propylene glycol |
| to pH 4.5 | Sodium hydroxide |
| ad 100 | Purified water |
| 8.50 g | Propellant blend. |

3. A method according to claim 1 wherein the propellant is butane, propane, isobutene, dimethylether, fluorocarbon gases or a mixture thereof.

4. A method according to claim 2, wherein the propellant is butane, propane, isobutene, dimethylether, fluorocarbon gases or a mixture thereof.

5. A method according to claim 2, wherein said foamable composition consists of

| | |
|---|---|
| 10.00 g/100 g | Caprylic/capric triglyceride |
| 1.20 g/100 g | Cetostearyl alcohol |
| 0.44 g/100 g | Glyceryl stearate |
| 0.10 g/100 g | Benzoic acid |
| 3.00 g/100 g | PEG-40 stearate |
| 0.08 g/100 g | Methylcellulose |
| 0.20 g/100 g | Xanthan gum |
| 1.00 g/100 g | Polysorbate 80 |
| 5.35 g/100 g | Dimethyl isosorbide |
| 12.00 g/100 g | Propylene glycol |
| to pH 4.5 | Sodium hydroxide |
| ad 100 | Purified water |
| 8.00 g | Propellant blend |

6. A method according to claim 2, wherein said foamable composition consists of

| | |
|---|---|
| 10.87 g/100 g | Caprylic/capric triglyceride |
| 1.09 g/100 g | Cetostearyl alcohol |
| 0.54 g/100 g | Glyceryl stearate |
| 0.10 g/100 g | Benzoic acid |
| 2.83 g/100 g | PEG-40 stearate |
| 0.11 g/100 g | Methylcellulose |
| 0.27 g/100 g | Xanthan gum |
| 0.98 g/100 g | Polysorbate 80 |
| 5.44 g/100 g | Dimethyl isosorbide |
| 10.87 g/100 g | Propylene glycol |
| to pH 4.5 | Sodium hydroxide |
| ad 100 | Purified water |
| 8.00 g | Propellant blend |

7. A method according to claim 2, wherein said foamable composition consists of

| | |
|---|---|
| 11.10 g/100 g | Caprylic/capric triglyceride |
| 0.90 g/100 g | Cetostearyl alcohol |
| 0.60 g/100 g | Glyceryl stearate |
| 0.11 g/100 g | Benzoic acid |
| 2.50 g/100 g | PEG-40 stearate |
| 0.15 g/100 g | Methylcellulose |
| 0.25 g/100 g | Xanthan gum |
| 0.90 g/100 g | Polysorbate 80 |
| 5.75 g/100 g | Dimethyl isosorbide |
| 11.80 g/100 g | Propylene glycol |
| to pH 4.5 | Sodium hydroxide |
| ad 100 | Purified water |
| 7.00 g | Propellant blend |

8. A method according to claim 2, wherein said foamable composition consists of

| | |
|---|---|
| 12.00 g/100 g | Caprylic/capric triglyceride |
| 1.00 g/100 g | Cetostearyl alcohol |
| 0.55 g/100 g | Glyceryl stearate |
| 0.12 g/100 g | Benzoic acid |
| 2.60 g/100 g | PEG-40 stearate |
| 0.18 g/100 g | Methylcellulose |
| 0.30 g/100 g | Xanthan gum |
| 0.95 g/100 g | Polysorbate 80 |
| 6.00 g/100 g | Dimethyl isosorbide |
| 12.25 g/100 g | Propylene glycol |
| to pH 4.5 | Sodium hydroxide |
| ad 100 | Purified water |
| 9.00 g | Propellant blend |

9. A method according to claim 2, wherein said foamable composition consists of

| | |
|---|---|
| 11.50 g/100 g | Caprylic/capric triglyceride |
| 1.20 g/100 g | Cetostearyl alcohol |
| 0.70 g/100 g | Glyceryl stearate |
| 0.15 g/100 g | Benzoic acid |
| 2.95 g/100 g | PEG-40 stearate |
| 0.20 g/100 g | Methylcellulose |
| 0.32 g/100 g | Xanthan gum |
| 1.20 g/100 g | Polysorbate 80 |
| 5.90 g/100 g | Dimethyl isosorbide |
| 11.50 g/100 g | Propylene glycol |
| to pH 4.5 | Sodium hydroxide |
| ad 100 | Purified water |
| 8.50 g | Propellant blend. |

10. A method according to claim 1, for the treatment of papulopustular rosacea.

* * * * *